US006973688B2

(12) United States Patent
Barker et al.

(10) Patent No.: US 6,973,688 B2
(45) Date of Patent: Dec. 13, 2005

(54) METHOD AND APPARATUS FOR MOVING AND LOCKING A MONITOR IN A PATIENT SUPPORT SYSTEM

(75) Inventors: David E. Barker, Salt Lake City, UT (US); Jeffrey W. Pattee, Salt Lake City, UT (US); John Matthew Simmons, West Jordan, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 186 days.

(21) Appl. No.: 09/682,860

(22) Filed: Oct. 25, 2001

(65) Prior Publication Data

US 2003/0079286 A1 May 1, 2003

(51) Int. Cl.[7] .................................................. A41F 7/00
(52) U.S. Cl. .............................................. 5/600; 5/658
(58) Field of Search ............................ 5/600, 617, 658, 5/503.1; 248/284.1, 123.11, 123.2, 280.11

(56) References Cited

U.S. PATENT DOCUMENTS

| | | | | |
|---|---|---|---|---|
| 4,768,241 A | * | 9/1988 | Beney | ........................... 5/600 |
| 4,852,842 A | * | 8/1989 | O'Neill | .................... 248/284.1 |
| 5,186,337 A | * | 2/1993 | Foster et al. | ................... 211/26 |
| 5,398,622 A | * | 3/1995 | Lubinskas et al. | ........... 108/145 |
| 5,542,138 A | * | 8/1996 | Williams et al. | ................ 5/658 |

* cited by examiner

Primary Examiner—Heather Shackelford
Assistant Examiner—Fredrick Conley
(74) Attorney, Agent, or Firm—McAndrews, Held & Malloy, Ltd.; Peter J. Vogel; Michael A. Dellapenna

(57) ABSTRACT

In accordance with at least one preferred embodiment of the present invention, a patient table is provided, the patient table comprising a patient support surface for supporting a patient during a medical procedure; a base supporting the patient support surface; a monitor displaying medical information relating to a medical procedure; and a pivot arm having a first end connected to the base and a second end connected to the monitor; a pivot release member provided on one of the monitor and the pivot arm for releasably securing the monitor and the pivot arm at predetermined angular positions with respect to the base.

20 Claims, 4 Drawing Sheets

METHOD AND APPARATUS FOR MOVING AND LOCKING A MONITOR IN A PATIENT SUPPORT SYSTEM

BACKGROUND OF INVENTION

At least one embodiment of the present invention generally relates to an adjustable monitor for patient tables for supporting patients during medical procedures. More particularly, at least one embodiment of the present invention relates to a movable mechanism that allows the monitor to move to different desired positions and locks the monitor in place.

Patient tables and monitors exist in a wide range of medical patient support systems for medical applications, each designed to be used for specific medical procedures. Medical patient support systems typically include two or three essential components, namely a patient support surface that is attached to a support apparatus. The support apparatus may include a mechanism for moving the patient table in various directions, including up and down, side to side, and/or into a sitting position. Typically monitors that are used in medical procedures are separate from the patient support system and are positioned on one side of the patient support system.

Conventional urology patient support systems support the patient in two positions, lying on their back and sitting up. A Urologist often needs to view a monitor while treating a patient. In such conventional systems a monitor is on one side of the patient. Urology procedures often require the patient and/or the doctor to be in more than one position. The desired position of the monitor, however, depends on the procedure being performed and the orientation of the doctor and patient relative to the equipment. The monitor therefore may be in an undesirable position or may be difficult to reposition during a procedure. There is a need therefore for a system that allows the monitor to be moved to different positions depending on the position of the patient and/or doctor. Additionally, there is a need for a monitor that can be easily moved and locked in the desired position.

Although monitors have been used with patient support systems, such monitors have not been easily movable to different positions. Prior systems also have not provided monitors that can be easily moved and locked into the desired position.

A need, therefore, exists for an improved medical patient support system that provides a patient table and monitor that may be easily moved and locked into different positions.

SUMMARY OF INVENTION

In accordance with at least one preferred embodiment of the present invention, a patient table is provided, the patient table comprising a patient support surface for supporting a patient during a medical procedure; a base supporting the patient support surface; a monitor displaying medical information relating to a medical procedure; and a pivot arm having a first end connected to the base and a second end connected to the monitor; a pivot release member provided on one of the monitor and the pivot arm for releasably securing the monitor and the pivot arm at predetermined angular positions with respect to the base.

One aspect of another embodiment of the present invention is a pivot release member with a handle section and a release trigger proximate one another to allow a user to grip the handle and release the trigger with the same hand to release the pivot arm and move the monitor relative to the base. Optionally the pivot release member is located on the end of the pivot arm proximate to the monitor.

One aspect of another embodiment of the present invention is a pivot arm that includes a fixed arm connected to the first end of the pivot arm and to the base.

One aspect of another embodiment of the present invention is a pivot release member further comprising a hydraulic spring for locking the pivot arm at predefined angular positions. Optionally the pivot release member further comprises a hydraulic spring for locking the pivot arm at the predefined angular positions and a hydraulic line extending between the hydraulic spring and a trigger proximate the monitor, the trigger selectively restricting the flow of hydraulic fluid through the hydraulic spring to lock the hydraulic spring at the predetermined angular positions.

One aspect of another embodiment of the present invention the patient table is a urological table.

One aspect of another embodiment of the present invention is the patient table including a patient support surface which will support a patient in at least two examination positions for a medical procedure, the pivot arm orienting the monitor in a first predetermined angular position parallel to the longitudinal axis of the table and another position at a second predetermined angular position perpendicular to the longitudinal axis of the table.

One aspect of another embodiment of the present invention is a patient table including a patient support surface which will support a patient in at least two examination positions, the pivot arm orienting the monitor at a predetermined angular position facing a side of the patient support surface and a second predetermined angular position facing an end of the patient support surface.

One aspect of another embodiment of the present invention is a urology table comprising a patient support surface with opposed ends along a longitudinal axis with opposed sides transverse to the longitudinal axis; a monitor displaying medical information relating to a medical procedure; a movable support member having a first end mounted to the patient support surface and a second end mounted to the monitor, at least one of the ends being movable relative to a corresponding one of the monitor and patient support surface to move the monitor between a first and second viewing positions, the monitor facing one of the sides when in the first viewing position, the monitor facing one of the ends when in the second viewing position.

One aspect of another embodiment of the present invention is a urology table comprising a patient support surface supporting a patient in at least two positions, a first position where the patient is lying horizontally on the patient support surface and the second position where the patient is sitting up vertically; a monitor displaying medical information relating to a medical procedure; a movable support member having a first end mounted to the patient support surface and a second end mounted to the monitor, at least one of the ends being movable relative to a corresponding one of the monitor and patient support surface to move the monitor between a first and second viewing positions, in a first viewing position the monitor facing one direction when the patient is vertical, and in the second viewing position the monitor facing perpendicular to the first viewing position when the patient is horizontal.

BRIEF DESCRIPTION OF DRAWINGS

The foregoing summary, as well as the following detailed description of the preferred embodiments of the present invention, will be better understood when read in conjunction with the appended drawings. For the purpose of illustrating the invention, there is shown in the drawings, embodiments which are presently preferred. It should be understood, however, that the present invention is not limited to the precise arrangements and instrumentality shown in the attached drawings.

DETAILED DESCRIPTION

Figure 1:
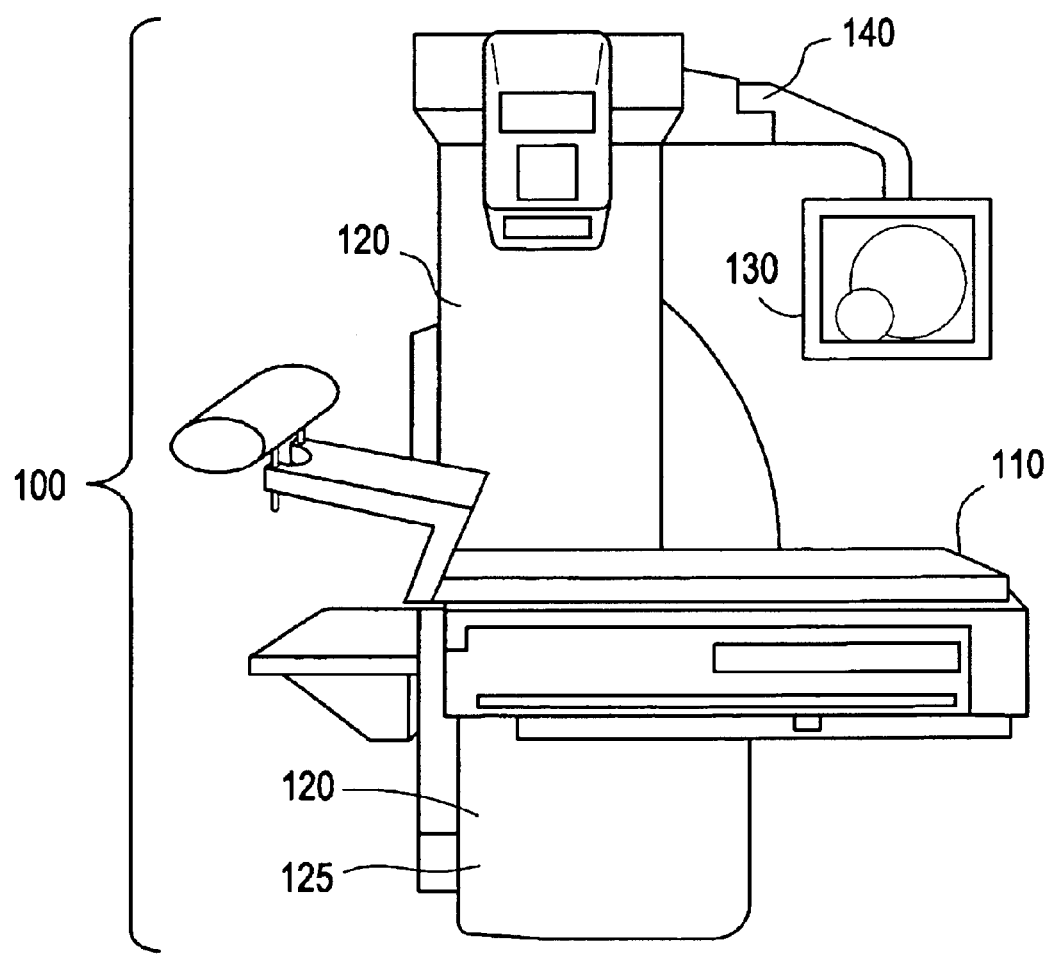
FIG. 1 illustrates a patient support system employing the monitor and moving mechanism according to one embodiment of the present invention.

FIG. 1 illustrates a patient support system 100 with a patient support surface 110, a base 120, a monitor 130 and a moving mechanism 140. The base 120 includes a support structure 125, which supports the patient support system 100. The patient support surface 110 is attached to and supported by the base 120. The monitor 130 is attached to the base 120 by the moving mechanism 140. The monitor 130 is preferably a flat screen monitor. The moving mechanism 140 supports the monitor 130. The moving mechanism 140 allows the monitor 130 to be moved and locked into different desired positions.

Figure 2:
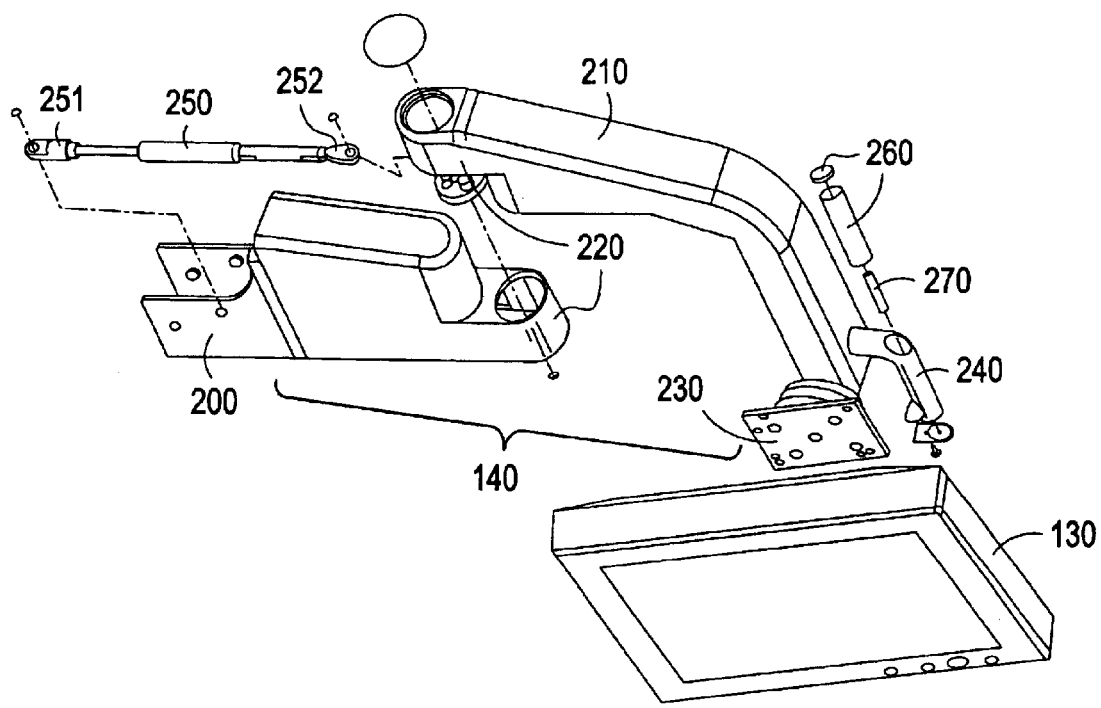
FIG. 2 illustrates a monitor and moving mechanism according to one embodiment of the present invention.

FIG. 2 illustrates the monitor 130 and moving mechanism 140 formed in accordance with one embodiment of the present invention. The moving mechanism 140 includes a fixed arm 200 and a pivot arm 210. The fixed arm 200 is connected to the base 120 of the patient support system 100 and may extend along a horizontal axis. The pivot arm 210 is angled, such as in an L-shape, and is connected at one end to the fixed arm 200 at the joint 220. The monitor 130 is attached to a plate 230 at the end of the pivot arm 210. A handle 240 is attached to the end of the pivot arm 210. The pivot arm 210 rotates the monitor 130 about the pivot axis, which is perpendicular to the monitor 130 plane. The pivot arm 210 lies in the pivot plane which contains the pivot axis.

A hydraulic spring 250 is located inside the fixed arm 200. The first end 251 of the hydraulic spring 250 is attached to the fixed arm 200. The second end 252 of the hydraulic spring 250 is connected to the joint 220 of the fixed arm 200 and pivot arm 210. The hydraulic spring 250 locks the pivot arm 210 in discrete positions. A release control 260 releases the hydraulic spring 250. When the hydraulic spring 250 is released the pivot arm 210 can move until the monitor 130 is in the desired position. As the monitor 130 is moved to the desired position, the hydraulic spring 250 is expanded or contracted. Once the release control 260 is released the hydraulic spring 250 locks the pivot arm 210. As shown in FIG. 2, in a preferred embodiment the hydraulic spring 250 release control 260 is located on the handle 240. The release control 260 is connected to a hydraulic line 270 which is routed through the pivot arm 210 and connected to the hydraulic spring 250 at the joint 220.

In a preferred embodiment the moving mechanism 140 may contain wires or cables for the monitor 130 or moving mechanism 140 within the fixed arm 200 and pivot arm 210. The joint 220 of the moving mechanism 140 may also be hollow to allow the wires or cables to remain within the moving mechanism 140.

In operation, the moving mechanism 140 is locked in place by the hydraulic spring 250. The user presses the release control 260 to release or unlock the hydraulic spring 250. As the user holds the release control 260 down the user may move the monitor 130 to the desired position. Once the monitor 130 is in the desired position the user releases the release control 260 and the hydraulic spring 250 locks the pivot arm 210 in place. The moving mechanism 140 therefore allows the monitor 130 to be moved and locked in any desired position with minimal effort.

Figure 3:
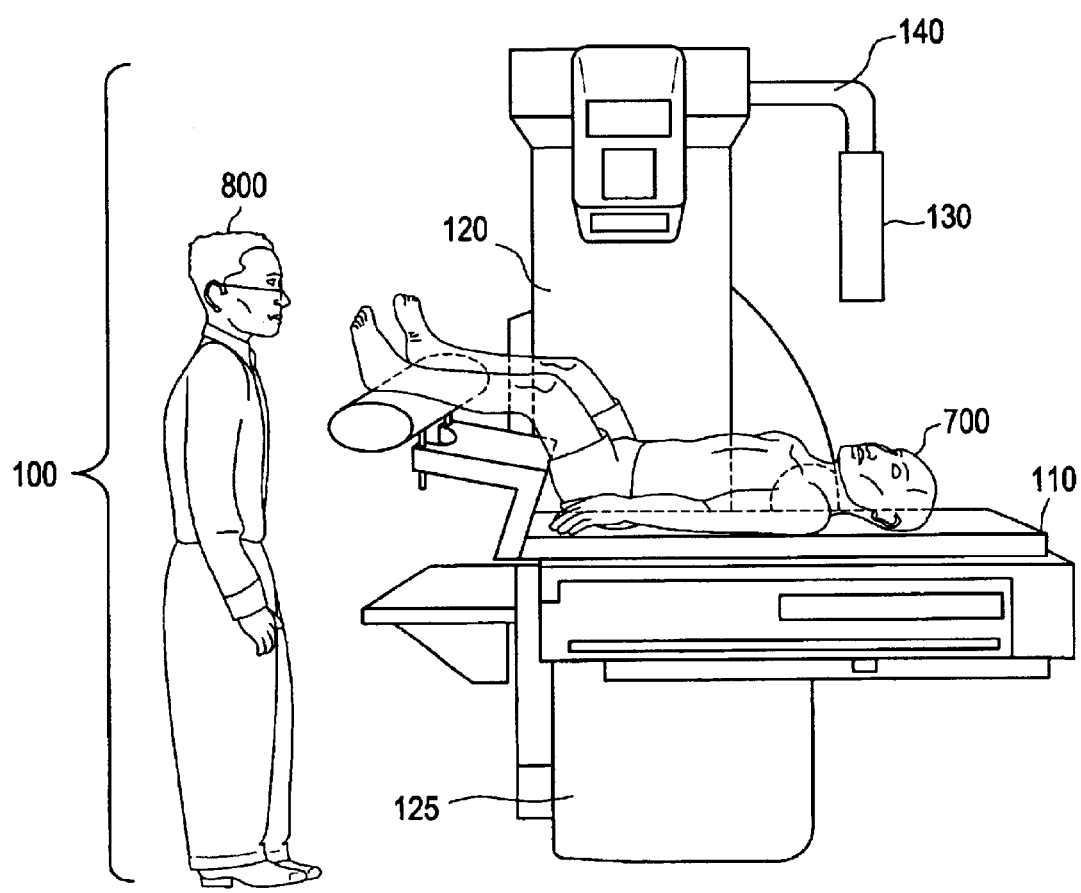
FIG. 3 illustrates a urology patient support system according to one embodiment of the present invention.
Figure 4:
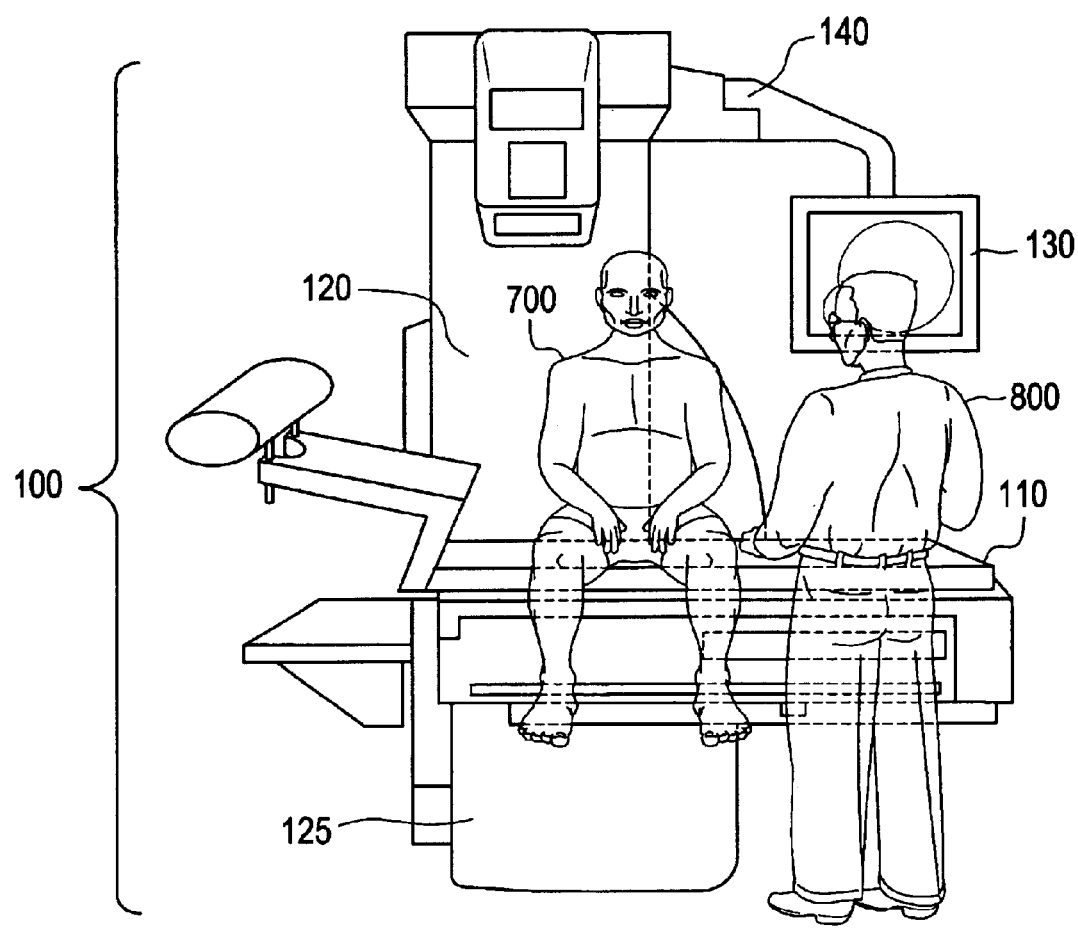
FIG. 4 illustrates a urology patient support system according to one embodiment of the present invention.

FIGS. 3 and 4 show, by way of example only, urology patient support systems 100 with two typical patient and doctor positions. In the first position, as shown in FIG. 3, the patient 700 is laying down on the patient support surface 110 and the doctor 800 is seated or standing near the legs of the patient 700. In this position, one desired monitor 130 location is over the patient's chest. In the second position, as shown in FIG. 4, the patient is sitting upright and the doctor is located at the patient's legs. In this position, one desired monitor 130 location is over the patient's head. A preferred embodiment of the present invention allows a doctor or another person to easily and safely move and lock the monitor 130 in multiple positions including the positions shown in FIGS. 3 and 4.

Optionally more than one fixed arm 200 and one pivot arm 210 may be used. Instead, additional fixed and/or pivot arms may be employed. For example, another pivot arm may be employed. In such a multi-pivot arm system, another hydraulic spring 250 may be included in the first pivot arm 210 to control and lock the additional pivot arm. In such a multi-pivot arm system, the release control 260 could control both pivot arms or another release control could be added so that each pivot arm 210 is released separately.

Optionally, the monitor 130 may be permitted to move in a direction other than horizontal. For instance, the pivot arm 210 could move vertically. Alternatively, the first pivot arm 210 could move horizontally and a second pivot arm could be added and oriented to move vertically, or vice versa. Alternatively, the fixed arm 200 could also be a first pivot arm. In such a system, the first pivot arm would be connected to the base 120 by a joint 220. In such a system, another hydraulic spring 250 may be included in the first pivot arm 210 to control and lock the first pivot arm 210. Again, in such a system, the release control 260 may control both pivot arms or a second release control may be added so that each pivot arm 210 is released separately.

Optionally, hydraulic springs 250 need not be used to lock the moving mechanism 140. Numerous mechanical devices or methods could be used as the moving mechanism 140.

The present invention may also be used in connection with the invention disclosed in U.S. patent application Ser. No. 09/682,859, and applicants hereby incorporate by reference application Ser. No. 09/682,859 in its entirety.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A patient table comprising:

a patient support surface for supporting a patient during a medical procedure;

a base supporting said patient support surface;

a monitor displaying medical information relating to a medical procedure;

a pivot arm having a first end connected to said base and a second end connected to said monitor; and a pivot release member provided on one of said monitor and said pivot arm for releasably securing said monitor and said pivot arm at predetermined angular positions with respect to said base, wherein said pivot release member includes a handle section and a release trigger proximate one another to allow a user to grip said handle and release the trigger with the same hand to release the pivot arm and move said monitor relative to said base;

wherein said patient table comprises a patient support surface which will support a patient in at least two examination positions for a medical procedure, said pivot arm orienting said monitor in a first predetermined angular position parallel to the longitudinal axis of the table and another position at a second predetermined angular position perpendicular to the longitudinal axis of the table.

2. The patient table of claim 1, wherein said monitor is over said patient in said second predetermined position.

3. The patient table of claim 1, wherein said pivot release member is located on the end of said pivot arm proximate to said monitor.

4. The patient table of claim 1, wherein said pivot arm further comprises a fixed arm connected to said first end of said pivot arm and to said base.

5. The patient table of claim 1, wherein said pivot release member further comprises a hydraulic spring for locking said pivot arm at said predefined angular positions.

6. The patient table of claim 1, wherein said pivot release member further comprises a hydraulic spring for locking said pivot arm at said predefined angular positions and a hydraulic line extending between said hydraulic spring and a trigger proximate said monitor, said trigger selectively restricting the flow of hydraulic fluid through said hydraulic spring to lock said hydraulic spring at said predetermined angular positions.

7. The patient table of claim 1, wherein said patient table is a urological table.

8. The patient table of claim 1, wherein said patient table comprises a patient support surface which will support a patient in at least two examination positions, said pivot arm orienting said monitor at a predetermined angular position facing a side of the patient support surface and a second predetermined angular position facing an end of the patient support surface.

9. The patient table of claim 1 wherein said pivot arm is a moving mechanism.

10. A patient table comprising:

a patient support surface for supporting a patient during a medical procedure;

a base supporting said patient support surface;

a monitor displaying medical information relating to a medical procedure;

a pivot arm having a first end connected to said base and a second end connected to said monitor; and a pivot release member provided on one of said monitor and said pivot arm for releasably securing said monitor and said pivot arm at predetermined angular positions with respect to said base, wherein said pivot release member further comprises a hydraulic spring for locking said pivot arm at said predefined angular positions;

wherein said patient table comprises a patient support surface which will support a patient in at least two examination positions for a medical procedure, said pivot arm orienting said monitor in a first predetermined angular position parallel to the longitudinal axis of the table and another position at a second predetermined angular position perpendicular to the longitudinal axis of the table.

11. A urology table comprising:

a patient support surface with opposed ends along a longitudinal axis with opposed sides transverse to said longitudinal axis;

a monitor displaying medical information relating to a medical procedure;

a movable support member having a first end mounted to said patient support surface and a second end mounted to said monitor, at least one of said ends being movable relative to a corresponding one of said monitor and patient support surface to move said monitor between a first and second viewing positions, said monitor facing one of said sides when in said first viewing position, said monitor facing one of said ends when in said second viewing position; and a hydraulic spring for locking said movable support member at, at least, one of said first and second viewing positions and a hydraulic line extending between said hydraulic spring and a trigger proximate said monitor, said trigger selectively restricting the flow of hydraulic fluid through said hydraulic spring to lock said hydraulic spring at, at least, one of said first and second viewing positions, wherein said monitor is over said patient in said second viewing position.

12. The urology table of claim 11, wherein said urology table further comprises a hydraulic spring for locking said movable support member at, at least, one of said first and second viewing positions.

13. The urology table of claim 11, wherein said movable support member comprises a fixed arm and a pivot arm.

14. The urology table of claim 11, wherein said urology table further comprises a release control remotely located that releases said movable support member.

15. A urology table comprising:

a patient support surface supporting a patient in at least two positions, a first position where the patient is lying horizontally on the patient support surface and the second position where the patient is sitting up vertically;

a monitor displaying medical information relating to a medical procedure;

a movable support member having a first end mounted to said patient support surface and a second end mounted to said monitor, at least one of said ends being movable relative to a corresponding one of said monitor and patient support surface to move said monitor between a first and second viewing positions, in a first viewing position said monitor facing one direction when the patient is vertical, and in said second viewing position said monitor facing perpendicular to said first viewing position when the patient is horizontal; and a release control remotely located that releases said movable support member, wherein said monitor is over said patient in said second viewing position.

16. The urology table of claim 15, wherein said urology table further comprises a hydraulic spring for locking said movable support member at, at least, one of said first and second viewing positions.

17. The urology table of claim 15, wherein said urology table further comprises a hydraulic spring for locking said movable support member at, at least, one of said first and second viewing positions and a hydraulic line extending between said hydraulic spring and a trigger proximate said monitor, said trigger selectively restricting the flow of hydraulic fluid through said hydraulic spring to lock said hydraulic spring at, at least, one of said first and second viewing positions.

18. The urology table of claim 15, wherein said movable support member comprises a fixed arm and a pivot arm.

19. A patient table comprising:
   a patient support surface for supporting a patient during a medical procedure;
   a base supporting said patient support surface;
   a monitor displaying medical information relating to a medical procedure;
   a pivot arm having a first end connected to said base and a second end connected to said monitor; and
   a pivot release member located on the end of said pivot arm proximate to said monitor for releasably securing said monitor and said pivot arm at predetermined angular positions with respect to said base;
   wherein said patient table comprises a patient support surface which will support a patient in at least two examination positions for a medical procedure, said pivot arm orienting said monitor in a first predetermined angular position parallel to the longitudinal axis of the table and another position at a second predetermined angular position perpendicular to the longitudinal axis of the table.

20. The patient table of claim 19, wherein said pivot release member includes a handle section and a release trigger proximate one another to allow a user to grip said handle and release the trigger with the same hand to release the pivot arm and move said monitor relative to said base; and wherein said pivot release member further comprises a hydraulic spring for locking said pivot arm at said predefined angular positions and a hydraulic line extending between said hydraulic spring and a trigger proximate said monitor, said trigger selectively restricting the flow of hydraulic fluid through said hydraulic spring to lock said hydraulic spring at said predetermined angular positions.

* * * * *